United States Patent [19]

Bernes et al.

[11] Patent Number: 5,372,143
[45] Date of Patent: Dec. 13, 1994

[54] BLOOD SAMPLING SYSTEM WITH LUER ADAPTOR

[75] Inventors: J. C. Bernes, Faimes; J. Debrauwere, Halle; M. Joie, Ernage; B. Van Breedam, Heverlee; J. M. Mathias, Lillois, all of

[73] Assignee: Baxter International Inc., Deerfield, Ill.

[21] Appl. No.: 979,567

[22] Filed: Nov. 20, 1992

[51] Int. Cl.⁵ .................................... A61B 5/00
[52] U.S. Cl. ........................................ 128/762
[58] Field of Search ............... 128/760, 762, 764, 766, 128/770; 604/244

[56] References Cited

U.S. PATENT DOCUMENTS

| | | | |
|---|---|---|---|
| 2,674,265 | 4/1954 | Dennis | 128/762 |
| 3,494,351 | 2/1970 | Horn | 128/762 |
| 3,696,802 | 10/1972 | Sausse | 128/762 |
| 3,730,170 | 5/1973 | Michael | 128/762 |
| 4,121,585 | 10/1978 | Becker, Jr. | 604/86 |
| 4,291,706 | 9/1981 | Voges et al. | 128/762 |
| 4,340,049 | 7/1982 | Munsch | 251/342 |
| 4,340,068 | 7/1982 | Kaufman | 604/244 |
| 4,392,850 | 7/1983 | Elias et al. | 604/88 |
| 4,392,851 | 7/1983 | Elias | 604/88 |
| 4,610,276 | 9/1986 | Paradis et al. | 137/856 |
| 4,676,256 | 6/1987 | Golden | 128/762 |
| 4,750,643 | 6/1988 | Wortrich | 604/80 |
| 4,819,684 | 4/1989 | Zaugg et al. | 137/112 |
| 4,911,696 | 3/1990 | Miyasaka et al. | 604/244 |
| 4,920,970 | 5/1990 | Wyatt | 128/762 |
| 4,931,049 | 6/1990 | Klimas | 604/83 |
| 4,999,307 | 3/1991 | Oakley | 128/762 |
| 5,045,067 | 9/1991 | Ohnaka et al. | 604/244 |
| 5,071,404 | 12/1991 | Larkin et al. | 604/86 |
| 5,097,842 | 3/1992 | Bonn | 128/762 |
| 5,098,406 | 3/1992 | Sawyer | 604/247 |
| 5,201,725 | 4/1993 | Kling | 604/284 |

FOREIGN PATENT DOCUMENTS 3941105  6/1991  Germany ............... 128/762

Primary Examiner—Max Hindenburg
Attorney, Agent, or Firm—Bradford R. L. Price; Paul C. Flattery; Robert M. Barrett

[57] ABSTRACT

A blood sampling system including a sampling device located in line is provided. The sampling device provides an access port that allows undiluted blood to be sampled automatically by insertion of a luer. The sampling device can have a number of different structures, for example, a swing valve, a ball valve, or a breakable seal for normally closing the sample port until a nozzle of the luer blood collector is forcibly inserted into the sample port.

11 Claims, 7 Drawing Sheets

BLOOD SAMPLING SYSTEM WITH LUER ADAPTOR

BACKGROUND OF THE INVENTION

The present invention relates to blood collection and sampling systems generally. More specifically, the present invention relates to systems for sampling blood directly from a donor during the collection process.

Of course, it is known to collect and use blood for a variety of treatments and therapies, e.g., transfusions. To effectively use collected blood it is necessary to test the blood to determine its type and other characteristics.

It is advantageous to sample blood directly from a donor rather than sample blood that is collected in a collection bag. An anticoagulant, or other solutions, are typically added to the blood in the collection bag. By sampling directly from the donor, undiluted blood, e.g., blood with no anticoagulant or other constituent, from the donor can be sampled.

A variety of techniques are used for this type of blood sampling. Such techniques are illustrated in FIGS. 1-4.

In one technique illustrated in FIG. 1, a tube 10 leading from a donor needle 11 to the primary collection bag (not illustrated) is clamped. Scissors are used to cut the tube on the collection bag side. The open end 12 of the tube 10 is then directed into a test tube 13 while releasing pressure on the clamp 14 to pour blood into the open test tube.

Another technique, illustrated in FIG. 2, utilizes an in-line intermediate needle 16 that is exposed by removing an in-line cover section 15 of the tube. An evacuated donor sampling tube 17 with a rubber stopper is connected to the needle 16. The needle 16 pierces the rubber stopper and blood flows into the sampling tube 17.

FIG. 3 illustrates another method of sampling blood. After the needle 18 is withdrawn from the donor's arm, the donor needle is used to pierce a rubber stopper of an evacuated test tube 19. A disadvantage of this system is that it does not sample blood from the donor but rather, samples blood, including an anticoagulant, from the primary collection bag 21.

FIG. 4 illustrates a still further method that involves using a Y-shaped branch connector 23 on the donor line 25 between the donor needle 27 and the primary collection bag (not shown). The outlet 33 of the Y connector include a connection system allowing filling of an evacuated test tube 35 through an adaptor 37.

There are a number of disadvantages with the prior art systems. For example, the use of scissors to cut the tubes creates the possibility for contamination of the system. Further, the prior art techniques that require the use of a needle add the potential risk of accidental needle sticks. Still further, some of the prior systems had the potential that sterility of the process could be compromised.

There is therefore a need for an improved method for sampling blood directly from the donor.

SUMMARY OF THE INVENTION

The present invention provides a system which allows one to sample undiluted blood directly from the donor. The system provides an easy technique to access the bloodstream in an aseptic way by the rupture of a frangible membrane, or the opening of a swing or ball valve. The method eliminates the use of scissors to open an end of a donor tube connected to a blood collection bag.

The system is designed to provide a sample port which fits with a luer connector, allowing the direct use of an evacuated tube holder system. Sterility of the sample port can be maintained until sampling.

Pursuant to the present invention, a collection system is provided for collecting blood at a first collection point from a donor. A sample system is provided for detouring a flow of said blood to a second collection point. The sample system includes an inlet that receives a flow of blood from the donor and a first outlet that delivers the blood flow to the first collection point. A second outlet, that is normally closed, but is openable by insertion of a sampling nozzle thereinto is provided for sampling blood.

Various embodiments of the sample member are provided pursuant to the present invention. In one embodiment the second outlet has a breakable seal, openable by insertion of the sample nozzle. In another embodiment, a ball valve is arranged to alternately open or close the first and second outlets. In another embodiment a swing valve is applied to the second outlet to simultaneously open said second outlet and close said first outlet, upon insertion of the sample nozzle.

An advantage of the present invention is that it provides an improved system for sampling blood directly from the donor.

Furthermore, an advantage of the present invention is that it provides a system that does not require a cutting of the tube to sample the blood.

Still further, an advantage of the present invention is that it provides a system for the direct use of an evacuated tube holder system.

Moreover, an advantage of the present invention is that it does not use unprotected needles that can cause accidental needle sticks.

Additionally, an advantage of the present invention is that it provides for the sterility of a conical fitting until the opening of the sterility barrier closure.

Additional features and advantages of the present invention are described in, and will be apparent from, the detailed description of the presently preferred embodiments and from the drawings.

BRIEF DESCRIPTION OF THE DRAWINGS

FIG. 10b illustrates a sectional view of the fitting shown in FIG. 10a;

DETAILED DESCRIPTION OF THE PRESENTLY PREFERRED EMBODIMENTS

The present invention provides systems for collecting blood and sampling undiluted blood from the patient. FIGS. 1 through 4 illustrate prior art systems and methods for sampling blood that the present invention improves upon.

Figure 1:
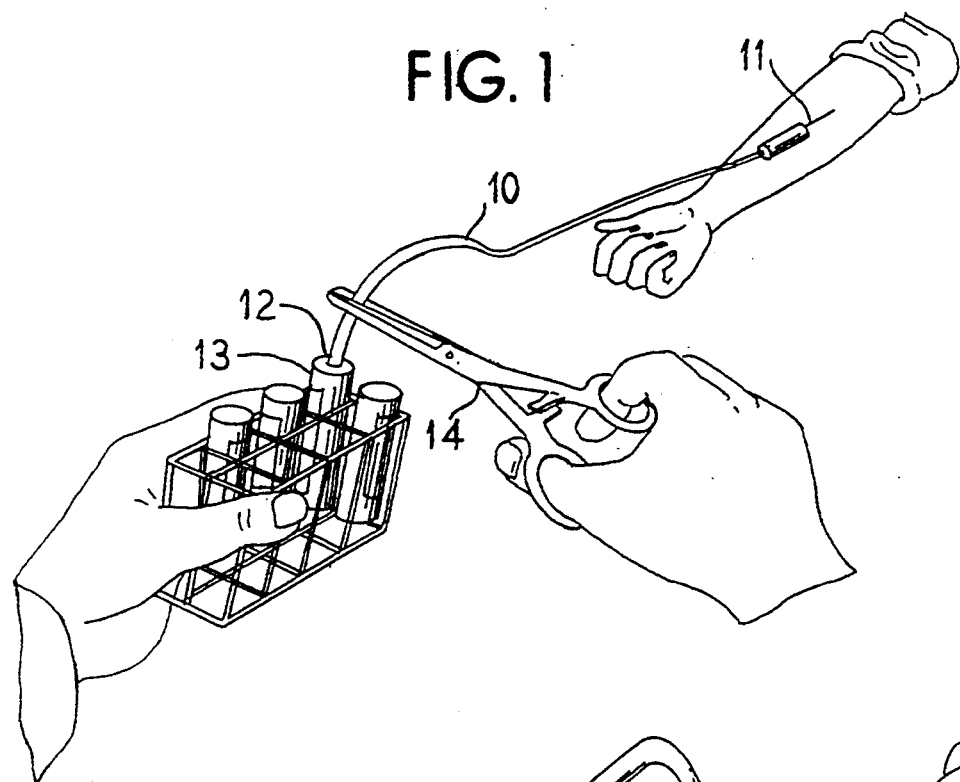
FIG. 1 illustrates a perspective view of a prior art system of sampling blood.
Figure 2:
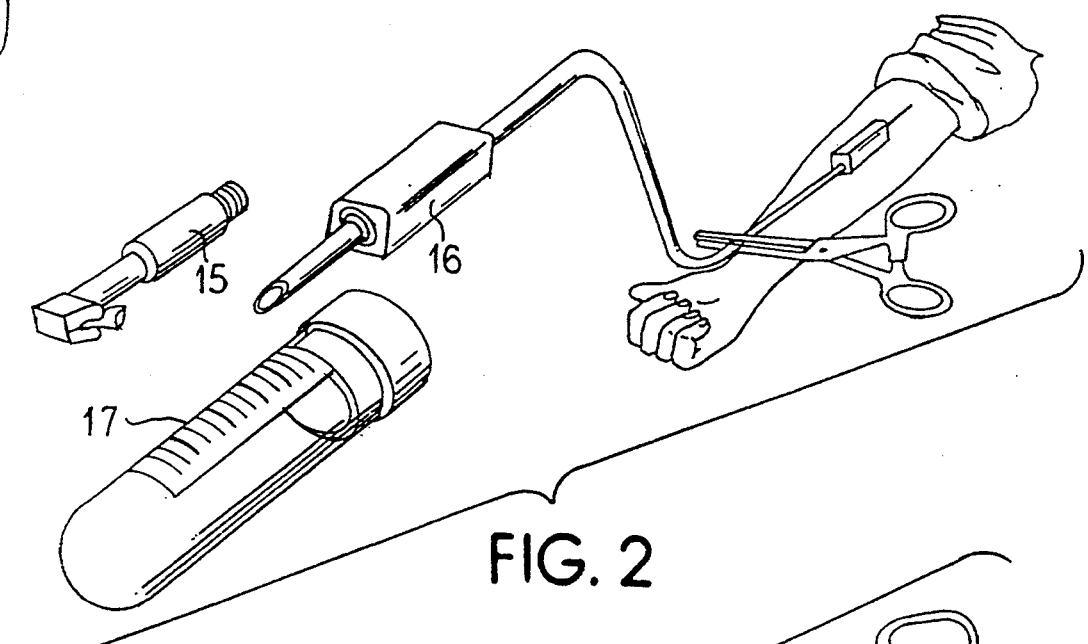
FIG. 2 illustrates an exploded perspective view of an alternate prior art method of sampling blood.
Figure 3:
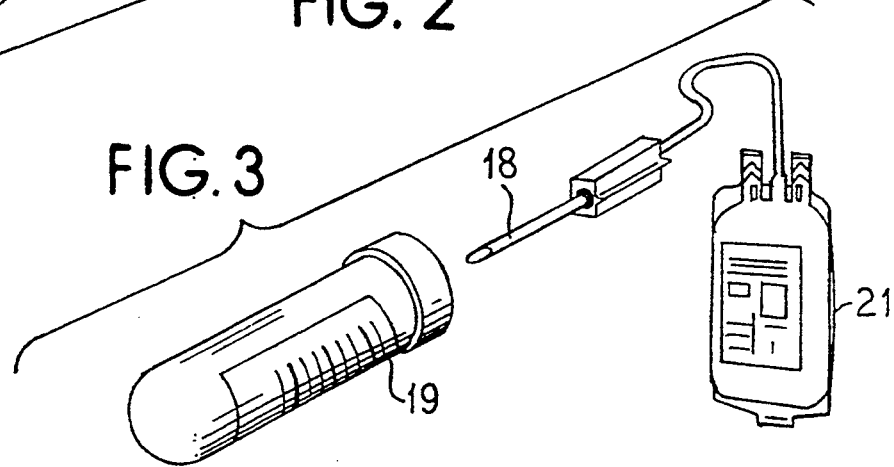
FIG. 3 illustrates an exploded perspective view of a further method in the prior art of sampling blood.
Figure 4:
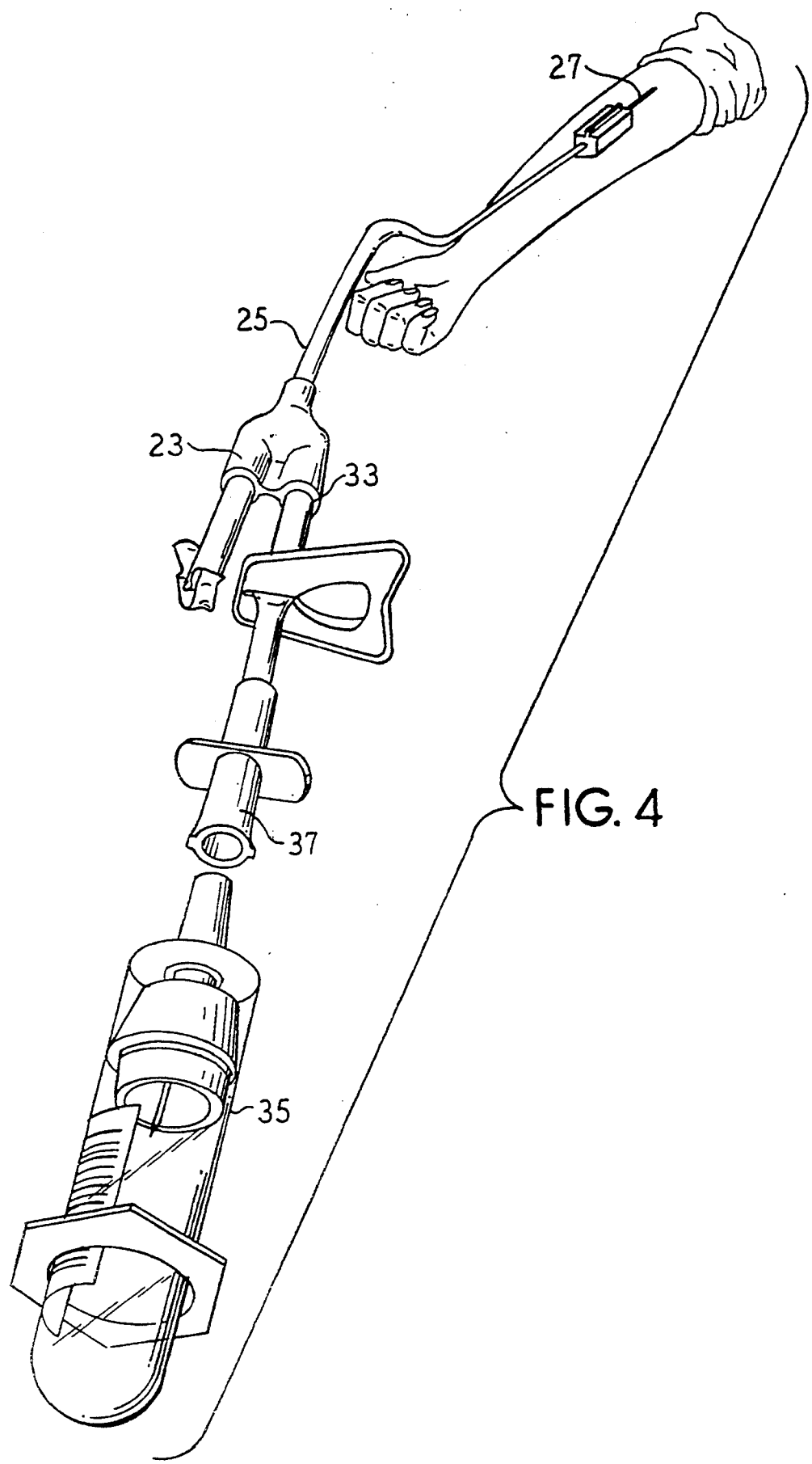
FIG. 4 illustrates an exploded perspective view of still further prior art method of sampling blood.
Figure 5:
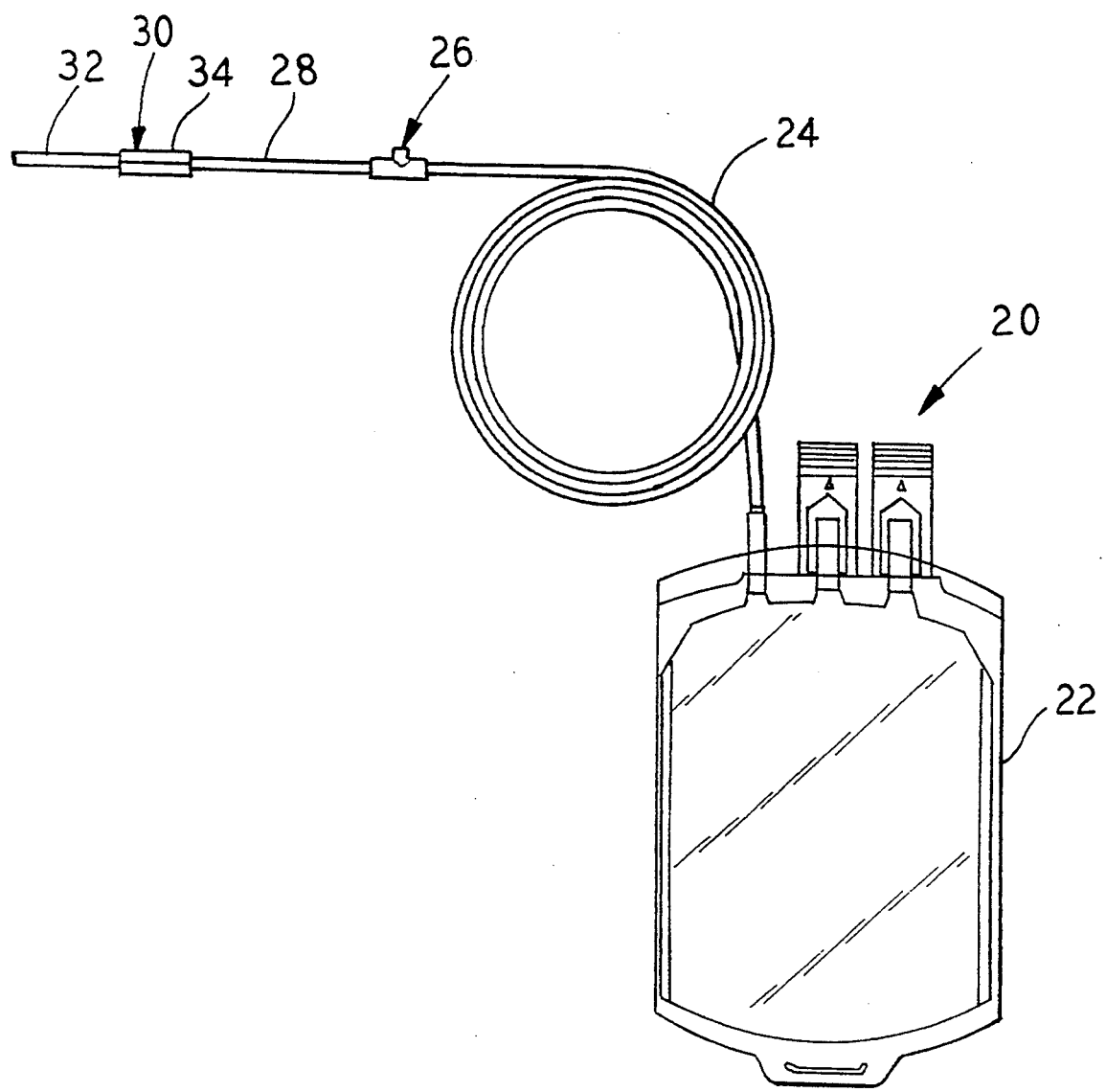
FIG. 5 illustrates a schematic elevational view of a blood sampling system of the present invention.

Referring now to FIG. 5, an embodiment of a blood collecting and sampling system 20 constructed pursuant to the present invention is illustrated comprising a collection bag 22, a donor tube 24 flow connected to the collection bag 22, a sample member 26, a sampling tube 28 connected to the sample member 26 and to a donor needle assembly 30. During collection of blood from a donor, blood flows from a donor's arm through a donor needle 32 through a needle connector 34 through the sample tube 28, through the sample member 26, through the donor tube 24 and into the collection bag 22.

Figure 6:
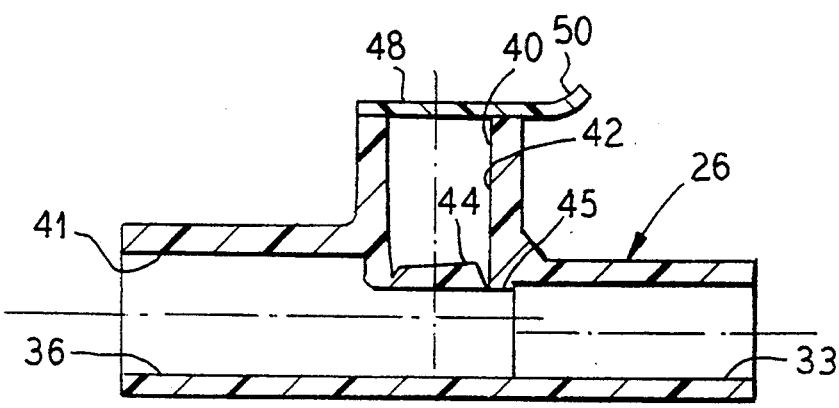
FIG. 6 illustrates a longitudinal sectional view of a sample device of the present invention.

FIG. 6 illustrates the sample member 26 of FIG. 5 in more detail. The sample member consists of a T-shaped part having an inlet 36 and a collection outlet 38 as well as a sample outlet 40. The inlet 36 and the collection outlet 38 are flow connected by a channel 41. The sample outlet 40 provides a female luer port 42 conically shaped and having a swing valve 44 arrayed therein. The swing valve can be hinged at a location 45, to the port 42. A sealed closure 48 is provided covering the sample outlet for maintaining the luer port 42 in a sterile condition. The closure 48 provides a tab 50 extending therefrom for peeling the closure 48 off of the sample outlet 40. The closure 48 can be secured to the outlet 40 by an adhesive.

Figure 7:
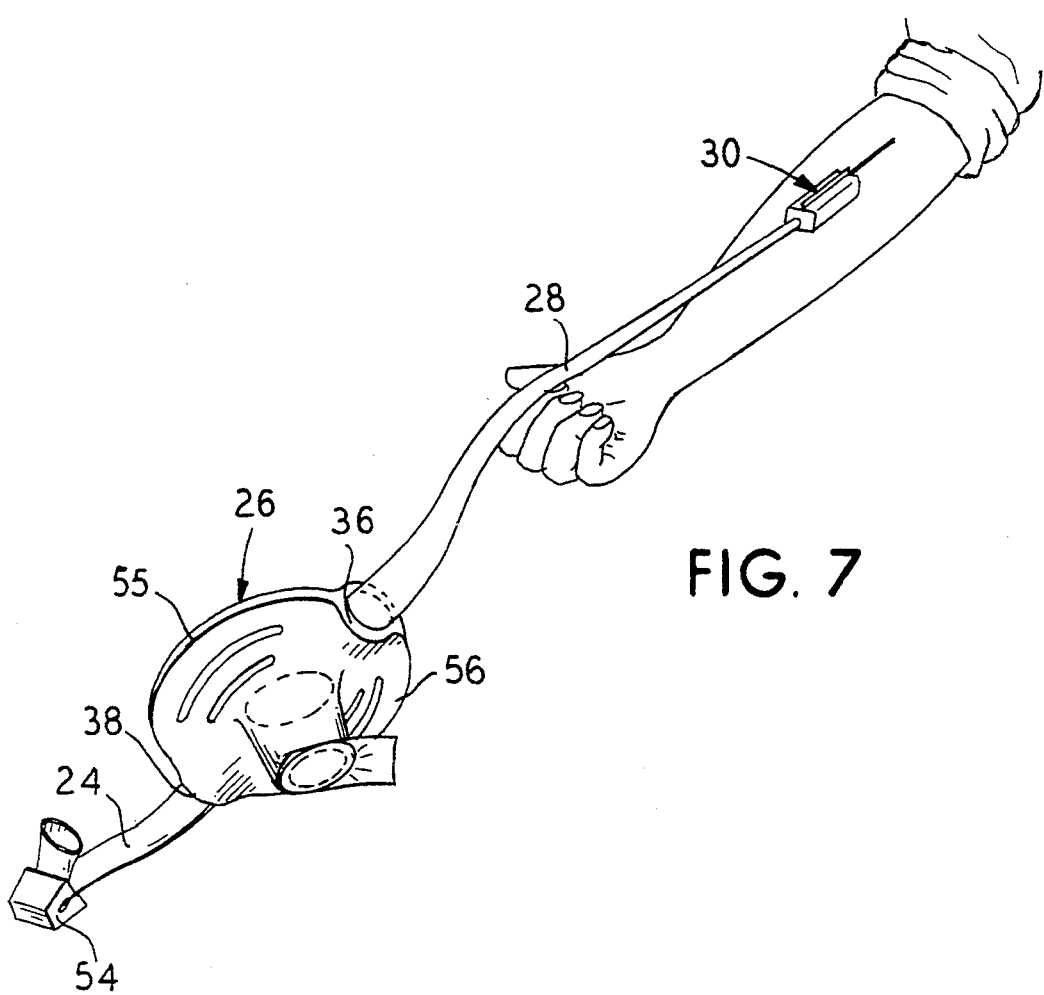
FIG. 7 illustrates a perspective view of the blood sampling system of FIG. 5 after separation of the collection bag.

Referring to FIG. 7, the sample member 26 is in position with a donor before sampling. The donor tube 24 has been cut from the container and clamped off with a clamp 54. Finger gripping wings 55, 56 extend outward from the inlet 36 and outlet 38 and provide a gripping surface for manipulating the sample member.

Figure 8:
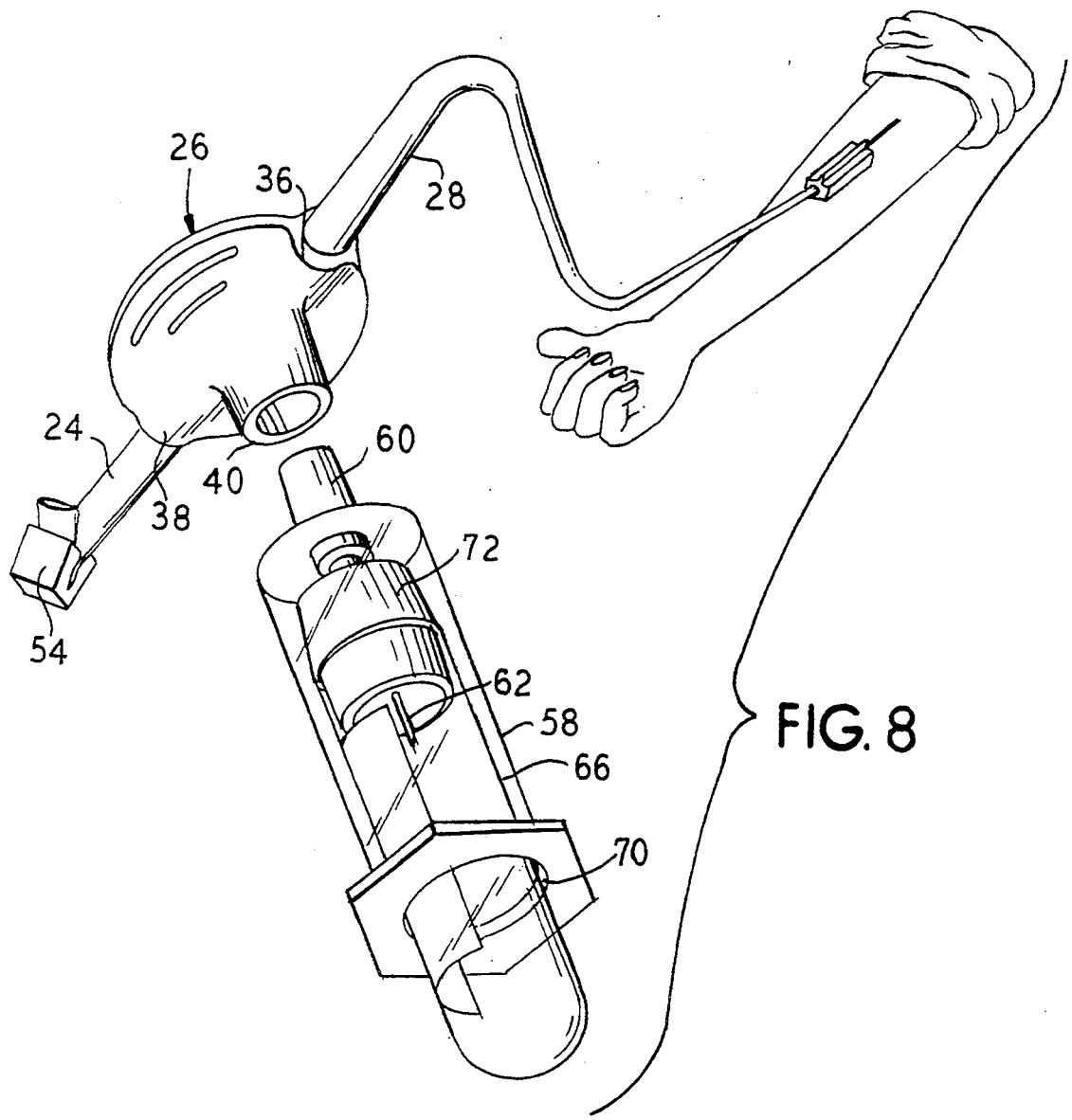
FIG. 8 illustrates an exploded perspective view of the blood sampling system of FIG. 7 with associated sampling tube.

As illustrated in FIG. 8, a tube holder 58 having a male luer nozzle 60, a needle 62 proceeding inwardly from the luer nozzle 60, receives a collection test tube 66 inserted into an open end 70 of the tube holder and having a stopper 72 covering an open end thereof. The needle 62 has pierced through the stopper in order to make a flow connection between the luer nozzle 60 and the evacuated sample tube 66. The closure 48 has been removed from the outlet 40.

Figure 9:
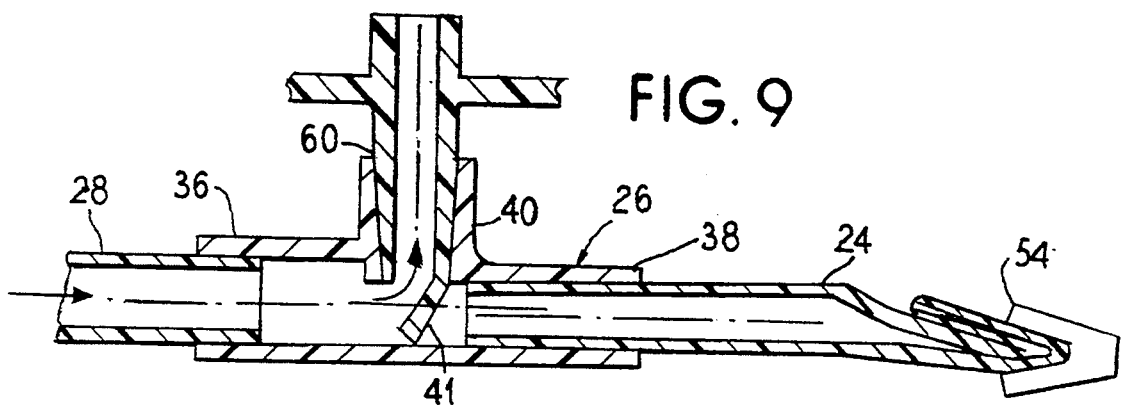
FIG. 9 illustrates a partial sectional view of the fitting and blood sample tube of FIG. 8.

FIG. 9 illustrates in sectional view the insertion of the nozzle 60 into the sample port 40 of the sample member 26. The swing valve 44 can initially be sealed in position blocking the sample port, 40 and the insertion of the male luer nozzle 60 breaks the seal and opens the swing valve 44. The luer nozzle 60 is inserted into the sample port 40 a sufficient distance to crack open the swing valve 44. The open swing valve then allows blood to flow from the inlet 36 through the sample port 40 through the luer nozzle 60 and into the test tube 66.

Figure 10A:
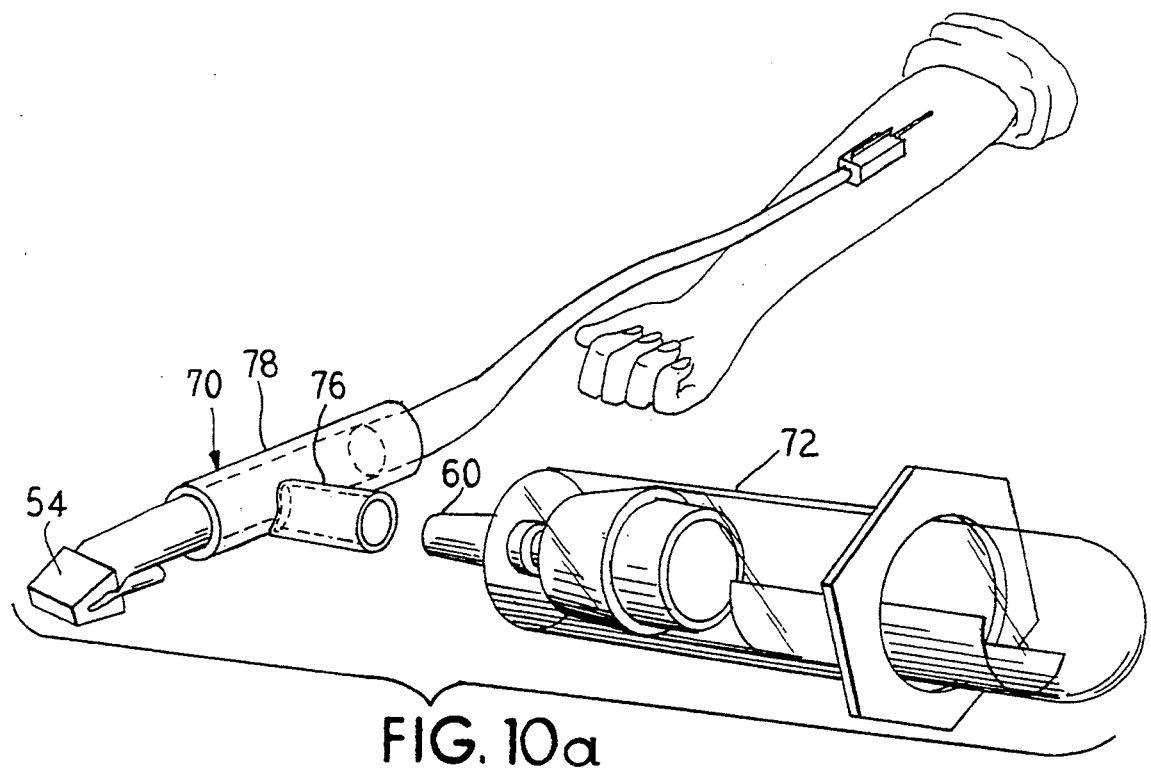
FIG. 10a illustrates an exploded perspective view of the blood sampling system of FIG. 5 with a different fitting.

Referring to FIG. 10a, another embodiment of the sample system including a sample member 70 is illustrated. The tube holder 58 and test tube 66, indicated as a unit 72, is identical to that of FIG. 8. The sample member has a sample port 76 arranged at an inclined angle from a main tubular body 78.

Figure 10B:
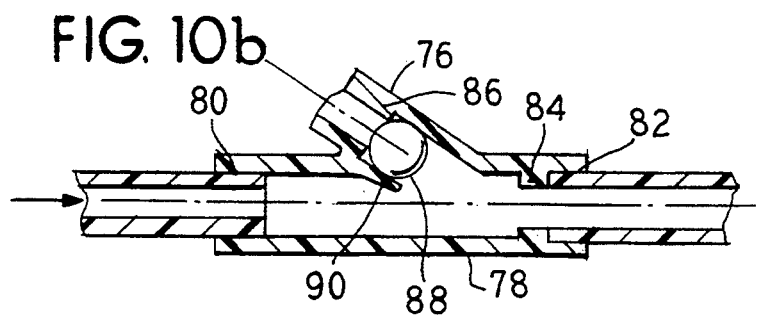

As illustrated in FIG. 10b, the main tubular body includes an inlet 80 and an outlet 82. Located recessed in the outlet 82 is a collar 84. The sample port 76 provides a collar or reduced diameter 86 adjacent its open end. Within the sample port 76 resides a ball valve 88 which, because of its diameter, cannot proceed outwardly of the collar 86 of the sample port 76. Also because of its diameter, the ball valve 88 cannot proceed past the collar 84 out of the outlet 82. Also, an edge 90 of the sample port 76 protruding into the main body 78 restricts the ball 88 from proceeding out of the inlet 80.

During donor collection into the collection bag, that is, blood flow out of the outlet 82, the ball valve 88 remains in the position of FIG. 10b which blocks blood flow out of the sample port 76. The diameter of the sample port 76 can be made sufficiently small to resiliently hold the ball valve tightly adjacent the collar 86 as shown in FIG. 10b. Alternately, the ball valve 88 can be initially sealed against the collar 86.

Figure 10C:
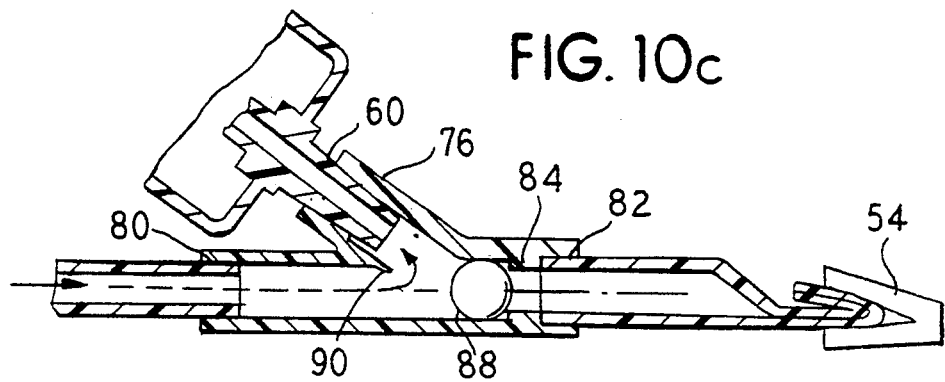
FIG. 10c illustrates a sectional view of the fitting of FIG. 10a with a sampling tube installed into the fitting.

FIG. 10c illustrates the orientation of the ball valve 88 during sampling. The male luer nozzle 60 is inserted into the sample port 76 which forces the ball valve 88 downward with respect to FIG. 10c causing a blood flow pathway to be opened between the inlet 80 and the sample port 76. Blood flow pressure impacting against the ball forces it further to the right against the collar 84 thus opening the pathway even further from the inlet 80 through the sample port 76 and into the collection tube.

As shown with regard to the embodiment of FIG. 6, a sealed closure, 48 having a tab 50 can also be applied over the sample port 76 to provide a sterility barrier during normal blood collection procedures into the collection bag or during storage. The cover 48 can be a plastic or other film material adhered to the sample port 76.

Figure 11C:
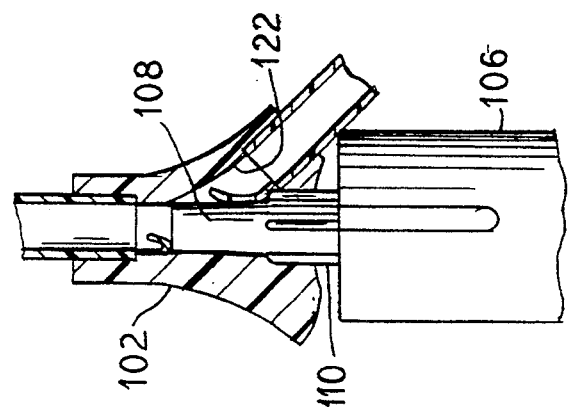
FIG. 11c illustrates a sectional view of the fitting of FIG. 11b with the collection tube holder fully inserted.
Figure 11B:
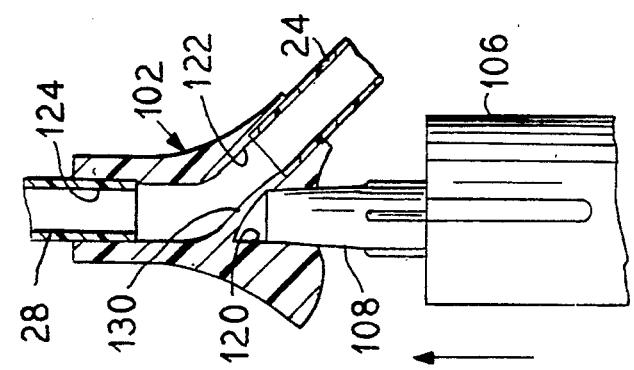
FIG. 11b illustrates a partial sectional view of the fitting of FIG. 11a with a collection tube holder partially engaged.
Figure 11A:
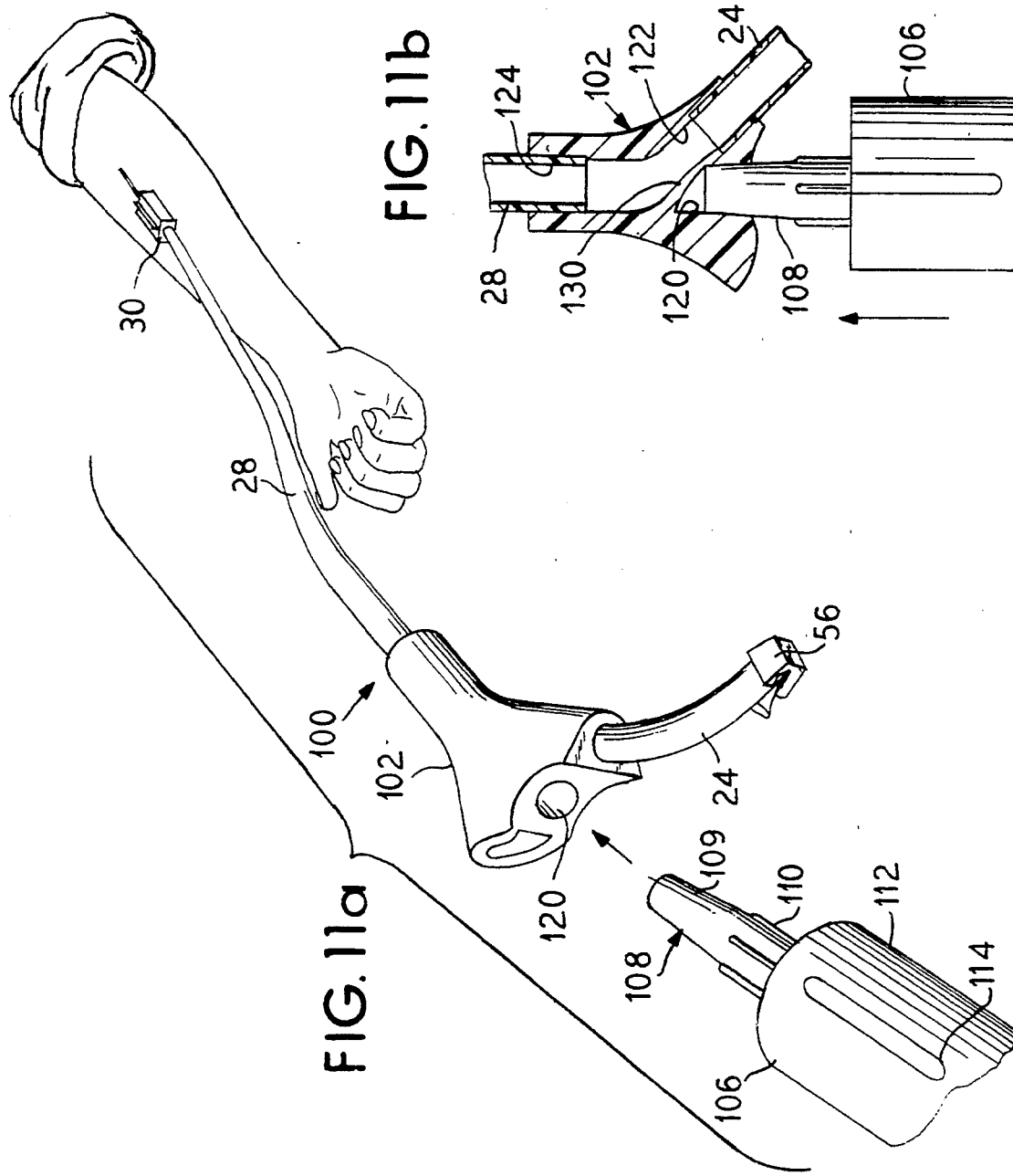
FIG. 11a illustrates a further embodiment of the blood sampling system of FIG. 5 wherein a different fitting is utilized.

Referring to FIG. 11a, another embodiment of the sampling system 100 of the present invention is illustrated. This system includes the needle assembly 30 and sample tube 28 of the previous described systems with a different sample member 102. During normal collection of the blood into a container (not shown) the donor tube 24 proceeding from the sample member 102 is used.

In FIG. 11a this tube 24 has been cut and clamped off with a clamp 56. For sampling, a luer assembly 106 is used. The luer comprises a male luer nozzle 108, having a conical lead end 109 and longitudinal ribs 110 at a base end thereof. The luer nozzle 108 is connected to a tube holder 106 which has a needle 114 proceeding inwardly, in flow connection with the male luer nozzle 108, An evacuated collection tube with a penetrable stopper (not shown) is then inserted into the tube holder whereby the needle 114 punctures the stopper. The sample member 102 includes a sample port 120 which receives the male luer nozzle 108 thereinto.

Referring to FIG. 11b, the sample member 102 is illustrated in more detail. The sample member has a outlet port 122 which is connected to the tube 24 for blood flow to the collection bag. The sample member has an inlet 124 which is shown connected to the sample tube 28. The outlet port 122 is angled off obliquely from the axis of the inlet 124. Arranged in axial alignment with the inlet 124 is the sample port 120. The sample port is normally closed with a recessed seal 130 which directs blood flowing from the inlet 124 to the outlet port 122. When the male luer nozzle 108 is inserted into the sample port 120 a sufficient distance, the seal 130 is broken.

As illustrated in FIG. 11c, the male luer nozzle 108 proceeds sufficiently into the sample member 102 to block off the outlet port 122 and for the ribs 110 to grip into the body of the sample member 102 to hold the tube holder 106 tightly thereto. The elasticity of the plastic material used for the molding of the sample member 102 allows tightness between the sample member and the male luer nozzle 108 with a partial penetration of the luer nozzle. The elasticity of the plastic material used for the molding of the sample system also allows introduction of the luer nozzle 108 a further distance to break the seal 130 and access the blood stream.

As shown with regard to the embodiment of FIG. 6, a sealed closure 48 having a tab 50 can also be applied over the sample port 120 to provide a sterility barrier during normal blood collection procedures into the collection bag or during storage. The cover 48 can be a plastic or other film material adhered to the sample port 120.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim as our invention:

1. A sampling device for use in a collection system for collecting blood from a donor, the sampling device comprising:
   a sample member including an elongate body having an inlet end with an inlet port and an opposed outlet end with an outlet port and a sample port, a blood collection channel defined in the body extending from the inlet port to the outlet port, a sampling channel defined in the body extending from the sample port to an inner end intersecting the blood collection channel at a point intermediate the length of the blood collecting channel, the inner end having a frangible membrane disposed thereat which normally closes off the sample channel from the blood collection channel, the frangible membrane being disposed in the body and configured so that a sampling nozzle may be inserted through the sample port to rupture the membrane and into the blood collection channel to close off flow to the outlet port and permit flow to the sampling nozzle whereby, a device permitting needleless access and direct sampling of the blood being collected is provided.

2. A sampling device as defined in claim 1, wherein the body is a molded plastic body.

3. A sampling device as defined in claim 1, wherein the body is a one-piece molded plastic body.

4. A sampling device as defined in claim 1, wherein the blood collecting channel includes an angle disposed therein intermediate the length thereof and defining a first collecting channel portion extending between the angle and the inlet port and a second collecting channel portion extending between the angle and the outlet port.

5. A sampling device as defined in claim 4, wherein the angle is disposed adjacent the inner end of the sample channel.

6. A sampling device as defined in claim 5, wherein the body includes a longitudinal axis and the inlet port, the first collecting channel portion, the sampling channel and the sample port are axially aligned along the longitudinal axis.

7. A sampling device as defined in claim 4, wherein the second collecting channel portion is disposed at an oblique angle with respect to the first collecting channel portion.

8. A sampling device as defined in claim 1, further comprising means for fluidly connecting the blood collection channel in-line in a blood collection set.

9. A sampling device as defined in claim 1, wherein the sample port and sample channel are resilient and provide gripping engagement of a sampling nozzle inserted in a sampling position therein.

10. A method for needleless sampling of blood being collected from a blood donor comprising the steps of:
    providing a blood collection set including a donor needle assembly, a collection bag, a sample member and donor tubing fluidly connecting the donor needle assembly to the ample member and the sample member to the collection bag, a sample member including a body having a generally Y-shaped configuration including an inlet end with an inlet port and an opposed outlet end with an outlet port and a sample port, a blood collection channel defined in the body extending from the inlet port to the outlet port, a sampling channel defined in the body extending from the sample port to an inner end intersecting the blood collection channel at a point intermediate the length of the blood collection channel, the inner end having a frangible membrane disposed thereat which normally closes off the sample channel from the blood collection channel;
    inserting the needle into a donor;
    permitting blood to flow from the needle through the donor tube, through the blood collection channel of the sample member and via tubing to the collection bag until collection in the collection bag is substantially complete;
    inserting a blood sampling nozzle through the sampling port a distance sufficient to cause rupture of the frangible membrane and to dispose the ample nozzle in fluidly connected engagement in the blood collection channel, thereby closing off flow to the outlet port of the sample member and providing needleless access to and direct sampling of donor blood being collected.

11. A method as defined in claim 10, wherein the sample port is sealed prior to use and the method further comprises the step of removing the seal on the sample port before inserting the blood sampling nozzle.

* * * * *